United States Patent
Yasuno et al.

(10) Patent No.: US 10,136,812 B2
(45) Date of Patent: Nov. 27, 2018

(54) OPTICAL COHERENCE TOMOGRAPHY APPARATUS FOR SELECTIVELY VISUALIZING AND ANALYZING VASCULAR NETWORK OF CHOROIDAL LAYER, AND IMAGE-PROCESSING PROGRAM AND IMAGE-PROCESSING METHOD FOR THE SAME

(71) Applicant: UNIVERSITY OF TSUKUBA, Tsukuba-shi, Ibaraki (JP)

(72) Inventors: Yoshiaki Yasuno, Tsukuba (JP); Lian Duan, Tsukuba (JP); Masahide Itoh, Tsukuba (JP)

(73) Assignee: UNIVERSITY OF TSUKUBA, Tsukuba-Shi (JP)

( * ) Notice: Subject to any disclaimer, the term of this patent is extended or adjusted under 35 U.S.C. 154(b) by 351 days.

(21) Appl. No.: 14/897,631

(22) PCT Filed: Jun. 10, 2014

(86) PCT No.: PCT/JP2014/065319
§ 371 (c)(1),
(2) Date: Dec. 10, 2015

(87) PCT Pub. No.: WO2014/199976
PCT Pub. Date: Dec. 18, 2014

(65) Prior Publication Data
US 2016/0135683 A1     May 19, 2016

(30) Foreign Application Priority Data
Jun. 13, 2013   (JP) ................................ 2013-124960

(51) Int. Cl.
*A61B 3/12* (2006.01)
*A61B 3/00* (2006.01)
(Continued)

(52) U.S. Cl.
CPC .......... *A61B 3/1233* (2013.01); *A61B 3/0025* (2013.01); *A61B 3/102* (2013.01);
(Continued)

(58) Field of Classification Search
CPC ......... A61B 3/0025; A61B 3/102; A61B 3/14; G01N 21/4795; G06T 2207/10101;
(Continued)

(56) References Cited

U.S. PATENT DOCUMENTS

| | | | | |
|---|---|---|---|---|
| 6,086,205 A | * | 7/2000 | Svetliza | A61B 3/1241 351/221 |
| 6,276,798 B1 | * | 8/2001 | Gil | A61B 5/0059 351/206 |

(Continued)

FOREIGN PATENT DOCUMENTS

| | | |
|---|---|---|
| JP | 11325849 A | 11/1999 |
| JP | 2002310897 A | 10/2002 |

(Continued)

OTHER PUBLICATIONS

International Search Report (ISR) dated Sep. 2, 2014, issued for International application No. PCT/JP2014/065319.

(Continued)

*Primary Examiner* — William R Alexander
*Assistant Examiner* — Grant A Gagnon
(74) *Attorney, Agent, or Firm* — Law Office of Katsuhiro Arai

(57) ABSTRACT

From OCT-measured data, only the image data of the choroidal vascular network present in the layer of the choroidal layer is selectively extracted, thereby accurately obtaining the thickness of the choroidal vessels and thickness of the choroidal vascular network from the image data, to allow for quantitative evaluation of the choroidal vascular network. The optical coherence tomography apparatus has (Continued)

an optical coherence tomography device, and a computer that processes the three-dimensional OCT tomographic images obtained based on the OCT-measured data acquired by the optical coherence tomography device. The computer functions as a means for selectively separating out only the images of the choroidal vessels from the three-dimensional OCT tomographic images to acquire image data of the choroidal vessels, and also as a means for obtaining the data to be used in the quantitative evaluation of the shape of the choroidal vessels based on the image data of the choroidal vessels.

12 Claims, 7 Drawing Sheets

(51) Int. Cl.
*A61B 3/14* (2006.01)
*A61B 3/10* (2006.01)
*G06T 7/00* (2017.01)
*G01N 21/47* (2006.01)

(52) U.S. Cl.
CPC .............. *A61B 3/14* (2013.01); *G06T 7/0012* (2013.01); *G01N 21/4795* (2013.01); *G06T 2207/10101* (2013.01); *G06T 2207/30041* (2013.01); *G06T 2207/30101* (2013.01)

(58) Field of Classification Search
CPC ......... G06T 7/0012; G06T 2207/30041; G06T 2207/30101
USPC .......................................................... 351/206
See application file for complete search history.

(56) References Cited

U.S. PATENT DOCUMENTS

| | | | |
|---|---|---|---|
| 9,875,570 B2* | 1/2018 | Gyger | ............... G06T 5/002 |
| 2012/0307014 A1 | 12/2012 | Wang | |
| 2015/0029464 A1* | 1/2015 | Jayasundera | ......... G06T 7/0016 351/246 |

FOREIGN PATENT DOCUMENTS

| JP | 2004028970 A | 1/2004 |
|---|---|---|
| JP | 2008039651 A | 2/2008 |
| JP | 2008175698 A | 7/2008 |
| JP | 2013518695 A | 5/2013 |
| JP | 2014104275 A | 6/2014 |

OTHER PUBLICATIONS

Joes.Staal et al., "Ridge-based vessel segmentation in color images of the retina,"IEEE Transactions on medical Imaging, Apr. 2004, vol. 23, No. 4, 501-509.
Kazuhiro Kurosawa, et al., "Three-dimensional retinal and choroidal capillary imaging bypower Doppler optical coherence angiography with adaptive optics", Sep. 24, 2012, Optics Express, vol. 20 No. 20, 22796-22812.
Li Zhang et al., "Automated segmentation of the choroid from clinical sd-oct," Nov. 2012, Invest. Ophthalmol. & Vis.Sci. vol. 53, No. 12, 7510-7519.
Lian Duan et al., "Automated segmentation and characterization of choroidal vessels in high-penetration optical coherence tomography", Jul. 1, 2013, Optics Express, vol. 21 No. 13, 15787-15808.
M. Martinez-Perez, et al.,"Retinal blood vessel segmentation by means of scale-space analysis and region growing," in"Medical Image Computing and Computer-Assisted Intervention IMIC-CAII9," 1999, vol. 1679, Lecture Votes in Computer Science, C. Taylor and A. Colchester, eds., Springer Berlin Heidelberg, pp. 90-97.
Marwan.D. Saleh et al., "An automated blood vessel segmentation algorithm using histogram equalization and automatic threshold selection," Aug. 2011, Journal of Digital Imaging, vol. 24, 564-572.
Nobuyuki Otsu, "A threshold selection method from gray-level histograms," Jan. 1979, IEEE Transactions on Systems, Man and Cybernetics, vol. 9, No. 1, 62-66.
Qin Li et al., "A multiscale approach to retinal vessel segmentation using gabor filters and scale multiplication," Systems, Man and Cybernetics, Oct. 8-11, 2006. IEEE International Conference on, 3521-3527.
Vedran Kajic et al., "Automated three-dimensional choroidal vessel segmentation of 3d 1060 nm oct retinal data," Jan. 1, 2013, Biomed. Opt. Express, vol. 4, 134-150.
Wenchao Cai et al.,"Multi-resolution vessel segmentation using normalized cuts in retinal images," 2006, Lecture Votes in Computer Science 4191, 928-936.
Youngjoo Hong et al., "Three-dimensional visualization of choroidal vessels by using standard and ultra-high resolutionscattering optical coherence angiography", Optics Express, Jun. 11, 2007, vol. 15 No. 12, 7538-7550.

* cited by examiner

[Fig. 1]
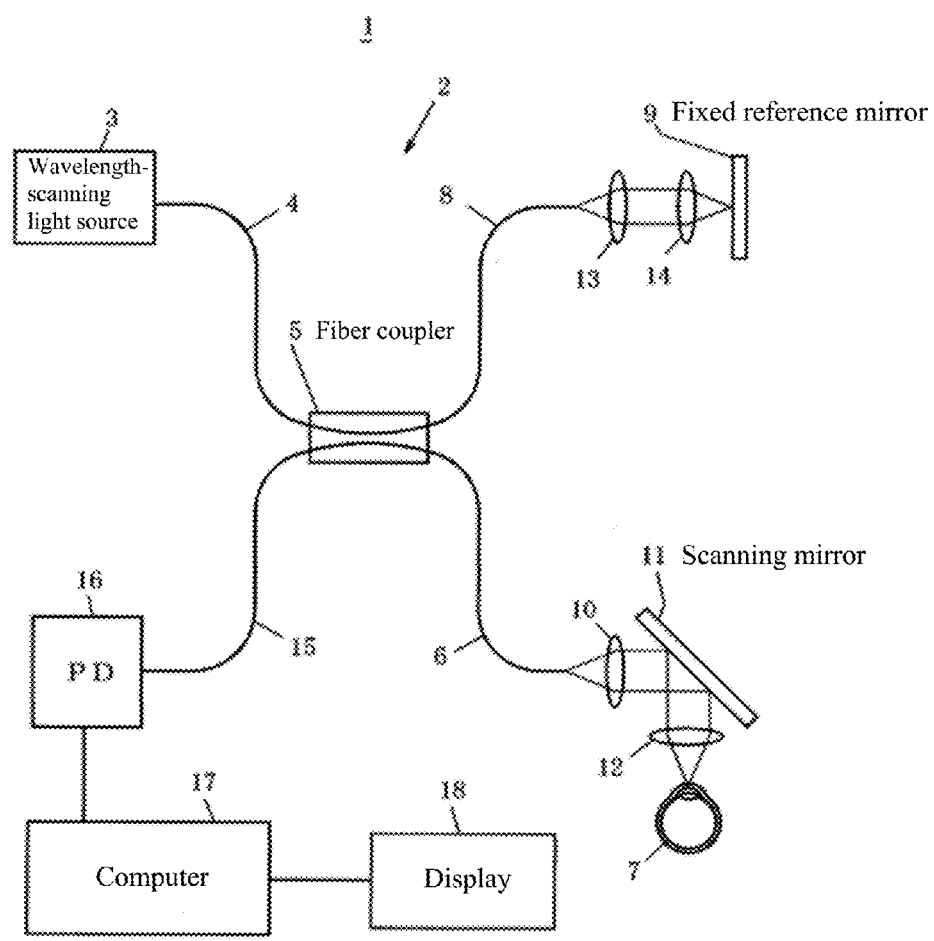

[Fig. 2]
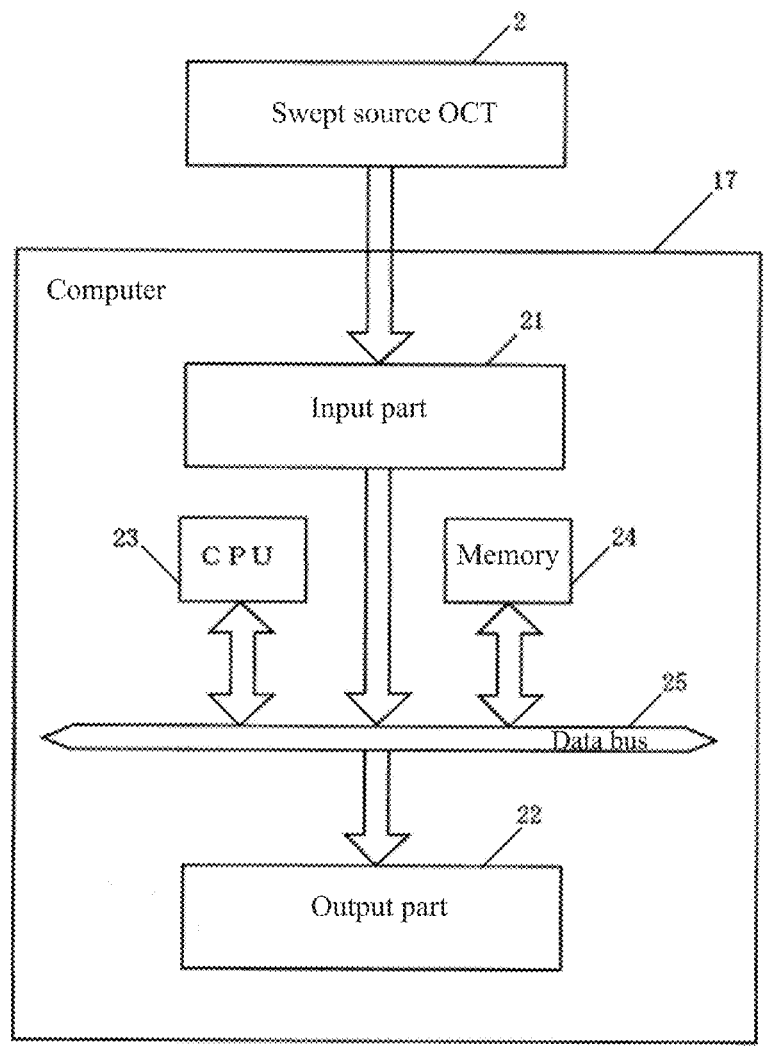

[Fig. 3]
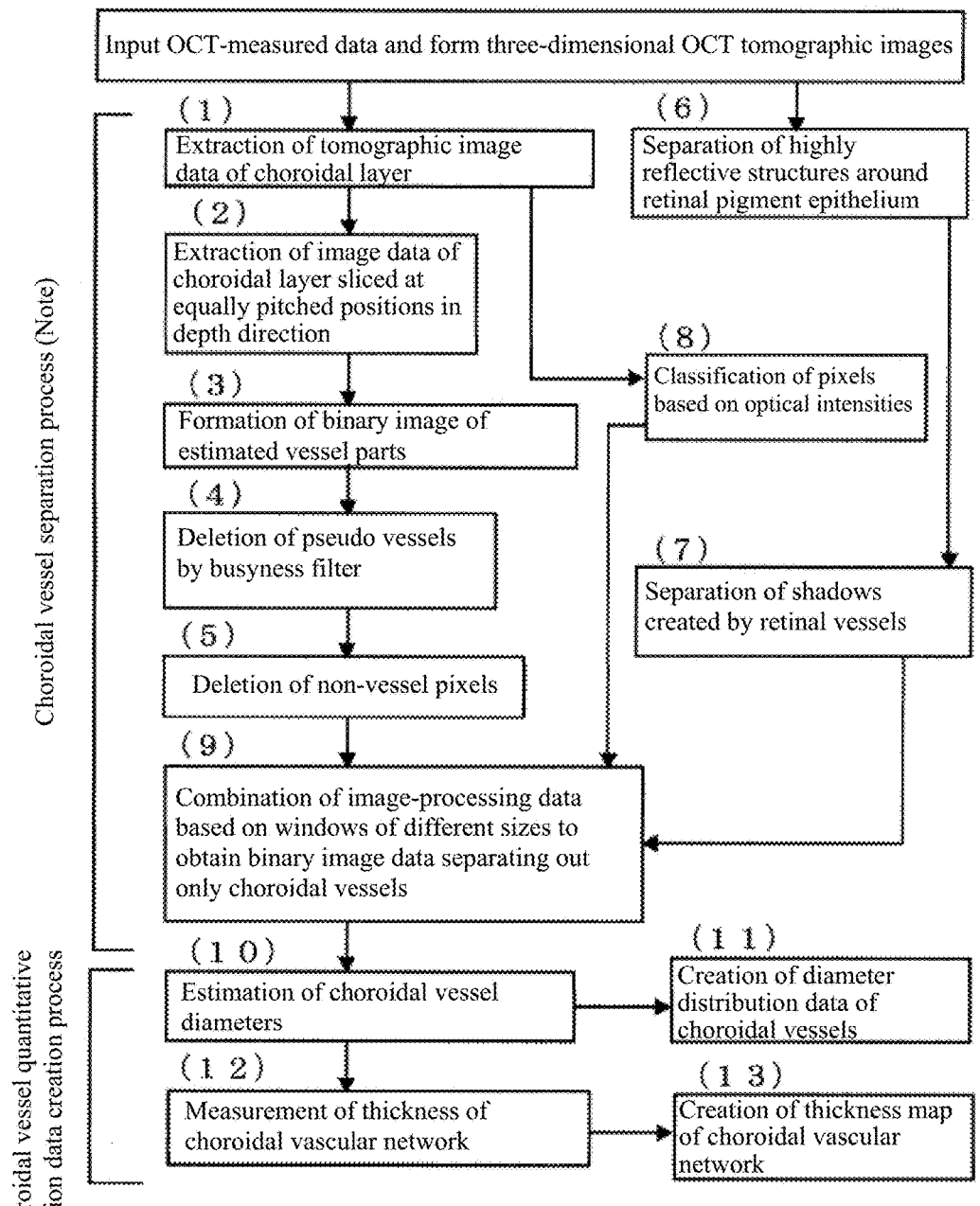
(Note) Steps (3) to (5) in the flow are performed for each of the windows of different sizes (47 μm, 94 μm, 188 μm, 375 μm).

[Fig. 4]
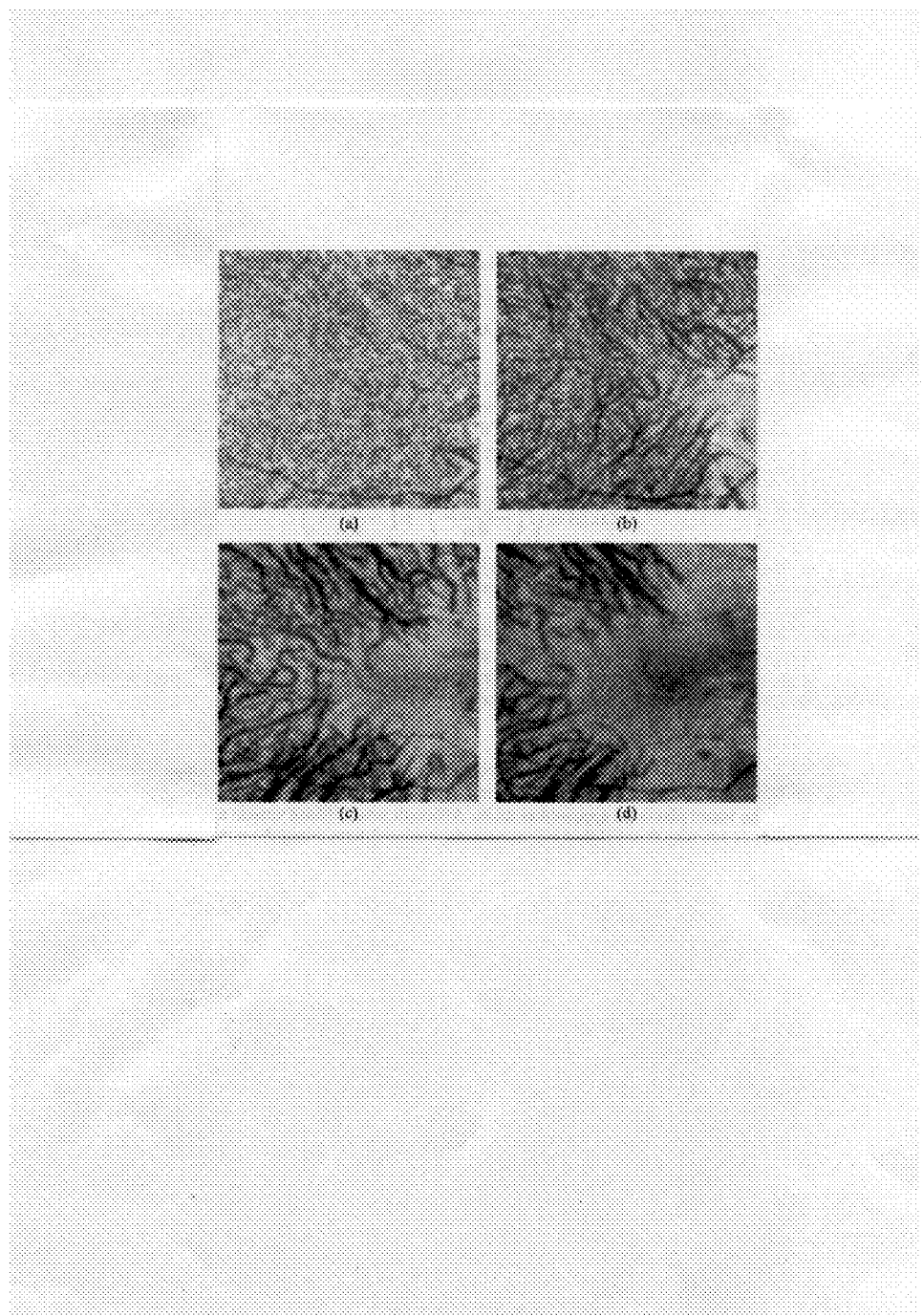

[Fig. 5]
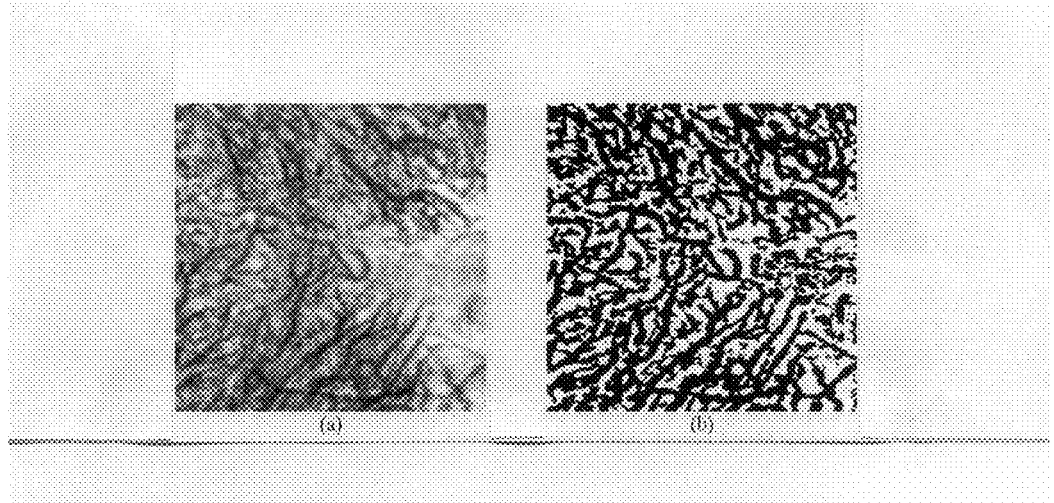
[Fig. 6]
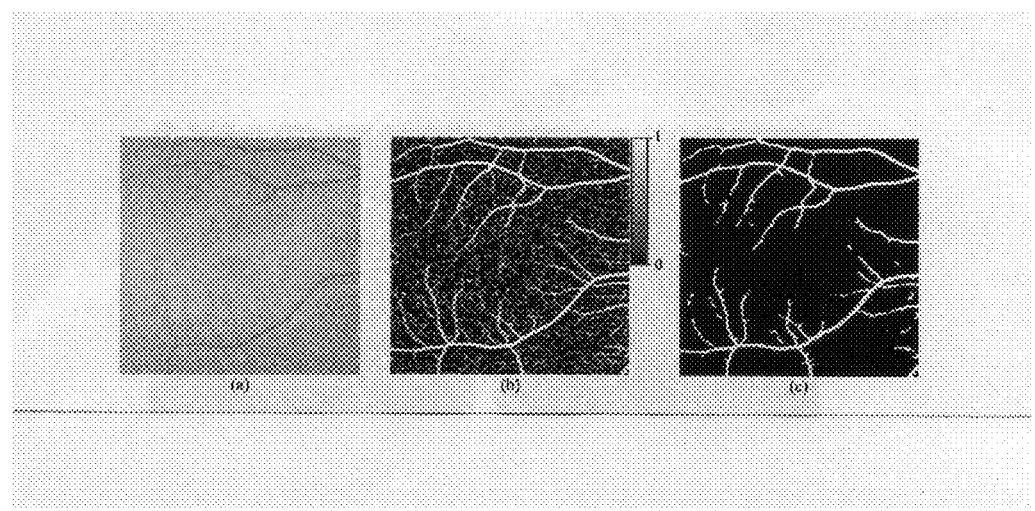

[Fig. 7]
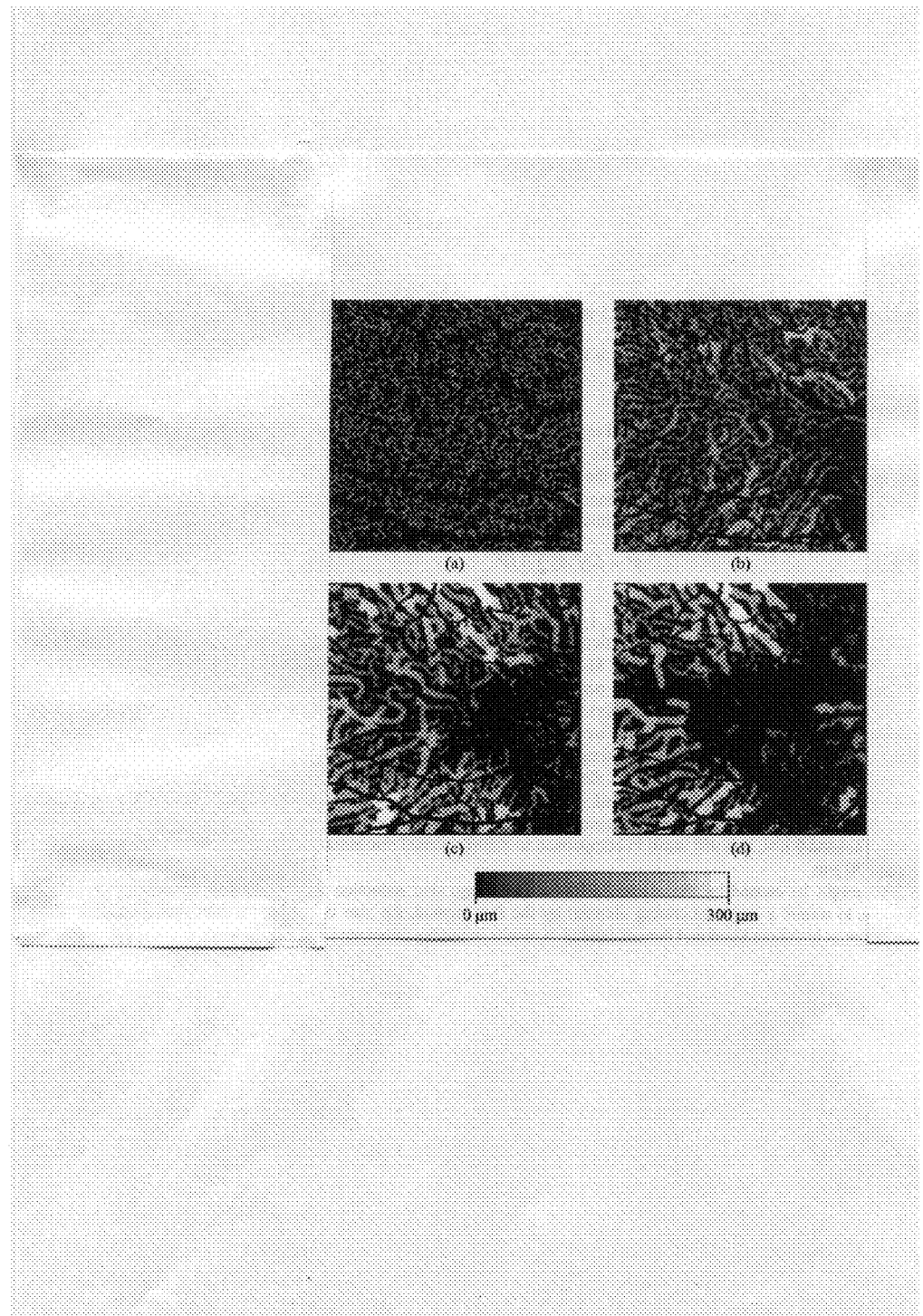

[Fig. 8]
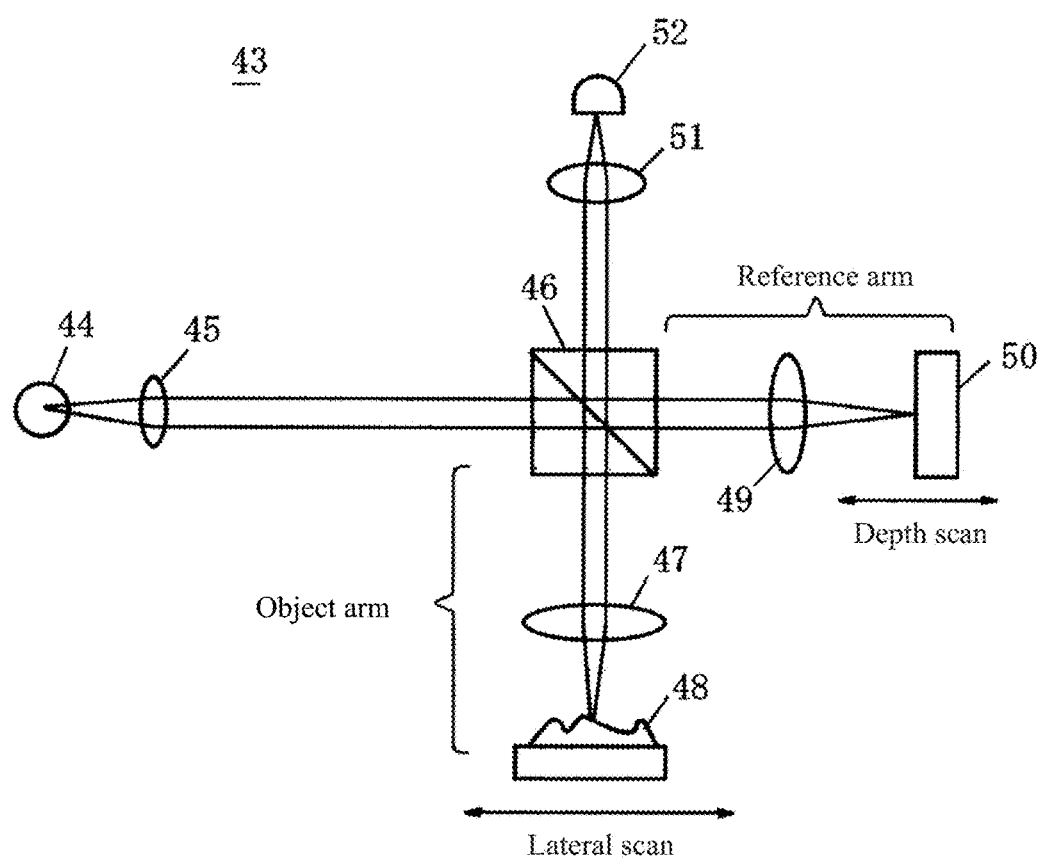

OPTICAL COHERENCE TOMOGRAPHY APPARATUS FOR SELECTIVELY VISUALIZING AND ANALYZING VASCULAR NETWORK OF CHOROIDAL LAYER, AND IMAGE-PROCESSING PROGRAM AND IMAGE-PROCESSING METHOD FOR THE SAME

This application is the U.S. National Phase under 35 U.S.C. § 371 of International Application PCT/JP2014/065319, filed Jun. 10, 2014, which claims priority to Japanese Patent Application No. 2013-124960, filed Jun. 13, 2013. The International Application was published under PCT Article 21(2) in a language other than English.

TECHNICAL FIELD

The present invention relates to an image-processing technology for images obtained by optical coherence tomography (abbreviated as "OCT") in the field of optical coherence measurement technology, and more specifically to an optical coherence tomography apparatus for visualizing and analyzing the choroidal vessels at the back of the eye, as well as an image-processing program and image-processing method therefor.

The aforementioned image-processing program under the present invention is summarized as having an algorithm for creating simulated angiographic images, that analyzes three-dimensional OCT tomographic images and builds simulated angiographic images of the back of the eye, as well as an algorithm for acquiring useful values (specifically the diameter of the choroidal layer and the thickness of the choroidal layer network) to quantitatively evaluate the vascular structure in the choroidal layer for diagnosis of diseases affecting the back of the eye, by further processing such simulated angiographic images of the back of the eye.

BACKGROUND ART

One non-invasive tomographic measuring technology that has been used in the medical field, etc., is an optical coherence tomography (OCT) that uses temporally low coherence light as a probe (refer to Patent Literature 1). The OCT, as it uses light as a measuring probe, has the advantage of being able to measure the refractive index distribution, spectrometric information, polarization information (double-refractive index distribution), etc., of the measuring target.

The basic OCT 43 is based on Michelson's interferometer and its principles are explained using FIG. 8. The light output from a light source 44 is parallelized by a collimator lens 45 and then split into reference light and object light by a beam splitter 46. The object light is condensed onto a measuring target 48 via an objective lens 47 inside the object arm, where the light is scattered and reflected and travels back to the objective lens 47 and beam splitter 46.

On the other hand, the reference light passes through an objective lens 49 inside the reference arm and then is reflected by a reference mirror 50 and travels back to the beam splitter 46 through the objective lens 49. The reference light, now back at the beam splitter 46, enters the focusing lens 51 together with the object light to be condensed onto a photodetector 52 (photodiode, etc.).

For the OCT light source 44, a source of temporally low coherence light (type of light that almost never interferes with another light output from the same light source at a different point in time) is used. With Michelson's interferometer that uses a temporally low coherence light as its light source, interference signals appear only when the distance from the reference arm and that from the object arm are roughly equal.

As a result, measuring the interference signal intensity using the photodetector 52 while changing the differential optical path length ($\tau$) between the reference arm and object arm gives interference signals relative to the differential optical path length (interferogram).

The shape of this interferogram represents the reflectance distribution in the depth direction of the measuring target 48, where the structure of the measuring target 48 in the depth direction can be obtained by one-dimensional axial scan. As described above, the OCT 43 allows for measurement of the structure of the measuring target 48 in the depth direction by means of optical path length scan.

This axial scan may be combined with lateral mechanical scan to obtain two-dimensional tomographic images of the measuring target using the resulting two-dimensional scan. The scanning device with which to perform this lateral scan may be constituted so that the measuring target is moved directly, or it may be constituted so that the objective lens is shifted while the target remains fixed, or it may be constituted so that both the measuring target and objective lens remain fixed while the galvano-mirror positioned near the pupillary surface of the objective lens is angularly rotated, or the like.

Extended forms of the aforementioned basic OCT are the spectral domain OCT (SD-OCT) where a spectrometer is used to obtain spectral signals, and the swept source OCT (SS-OCT) designed to obtain spectral interference signals by scanning the wavelength of the light source. The SD-OCT is classified into the Fourier domain OCT (FD-OCT; refer to Patent Literature 2) and the polarization-sensitive OCT (PS-OCT; refer to Patent Literature 3).

The FD-OCT is characterized in that the wavelength spectra of reflected light from the measuring target are obtained using a spectrometer, after which the obtained spectral intensity distribution is Fourier-transformed to retrieve the signals in real space (OCT signal space), and with this FD-OCT, the tomographic structure of the measuring target can be measured by scanning it in the x-axis direction, without scanning it in the depth direction.

The SS-OCT obtains three-dimensional optical tomographic images by changing the wavelength of the light source using a high-speed wavelength-scanning laser and then rearranging interference signals and thus processing the signals using the light source scan signals synchronously obtained by the spectral signals. Those using a monochrome meter as the means for changing the wavelength of the light source can also be used as the SS-OCT.

Measuring the distribution of retinal blood flows using the Doppler optical coherence tomography (Doppler OCT) has been known. This provides a means for measuring the distribution of retinal blood flows using the aforementioned FD-OCT, etc., and similarly for forming cross-sectional images of retinal blood flows as well as observing the three-dimensional vascular channel structure of the retina using the spectral domain OCT.

The inventors of the present invention had previously focused on the Doppler OCT and studied/developed methods to non-invasively measure in-vivo blood flows, particularly those at the back of the eye. The inventors of the present invention had previously succeeded in examining the blood flows at the back of the eye by implementing the Doppler OCT based on the SD-OCT technology, but in recent years the technological base of OCT has been shifting from the SD-OCT to the next-generation OCT, namely, SS-OCT.

One social issue of late is that many cases of glaucoma and age-related macular degeneration (AMD) are being reported among other ophthalmological diseases, and it has become important to find technology to quantitatively evaluate the data measured on tomographic images of the back of the eye for effective diagnosis and treatment of these diseases.

At the back of the eye, the choroidal layer is a layer having many blood vessels (choroidal vessels) present between the retinal pigment epithelium (RPE) and sclerotic coat. Also, the choroidal layer has a function to supply oxygen and nutrients to the outer layer of the retina. Morphological changes to the choroidal vessels are useful in diagnosing glaucoma, age-related macular degeneration (AMD), and other eye diseases associated with circulatory anomaly. In this sense, images of the choroidal vessels are extremely useful in the field of ophthalmology.

Indocyanine green angiography (ICGA) has been traditionally used as a standard means for imaging the choroidal vessels, and use of near infrared light and near infrared light detector achieves greater permeability than when fluorescence angiography is used.

Incidentally, in diagnosing glaucoma, age-related macular degeneration (AMD), and other diseases mentioned above, it is necessary to separate out and distinguish blood vessels, and for this reason many algorithms for separating out the vessels shown on two-dimensional or three-dimensional images have been proposed (refer to Non-patent Literatures 1 and 2).

Separated images of choroidal vessels not only provide intuitively visual pictures of the choroidal vessels, but they also provide quantitative information of their morphology, which is useful in understanding the pathologies of eye diseases associated with blood flows.

Normally, blood vessels are identified using two different means: the tracking-based means (refer to Non-patent Literature 3) and the window-based means (refer to Non-patent Literatures 4 and 5). The tracking-based means is a time-consuming method involving tracing the areas where blood vessels must be extracted, while the window-based means that detects blood vessel boundaries, etc., using a filter requires further improvement of image accuracy.

Recently, a method for automatically extracting the choroidal vessels using etiological detection and regional growth technology was developed, and 3D images have been obtained and the choroidal vessels have been extracted using this method (refer to Non-patent Literature 6).

In addition, a means for automatically separating out blood vessels using a multi-scale 3D edge filter has been proposed (refer to Non-patent Literature 7).

BACKGROUND ART LITERATURE

Patent Literature

Patent Literature 1: Japanese Patent Laid-open No. 2002-310897
Patent Literature 2: Japanese Patent Laid-open No. Hei 11-325849
Patent Literature 3: Japanese Patent Laid-open No. 2004-028970

Non-Patent Literature

Non-patent Literature 1: M. Martinez-Perez, A. Hughes, A. Stanton, S. Thom, A. Bharath, and K. Parker, "Retinal blood vessel segmentation by means of scale-space analysis and region growing," in "Medical Image Computing and Computer-Assisted Intervention 1MICCA119,", vol. 1679 of Lecture Notes in Computer Science, C. Taylor and A. Colchester, eds. (Springer Berlin Heidelberg, 1999), pp. 90-97.
Non-patent Literature 2: J. Staal, M. Abramoff, M. Niemeijer, M. Viergever, and B. van Ginneken, "Ridge-based vessel segmentation in color images of the retina," IEEE Trans. Med. Imag. 23, 501-509 (2004).
Non-patent Literature 3: W. Cai and A. C. S. Chung, "Multi-resolution vessel segmentation using normalized cuts in retinal images," Lecture Notes in Computer Science 4191, 928-936 (2006).
Non-patent Literature 4: Q. Li, J. You, L. Zhang, and P. Bhattacharya, "A multiscale approach to retinal vessel segmentation using gabor filters and scale multiplication," Systems, Man and Cybernetics, 2006. SMC '06, IEEE International Conference on 4, 3521-3527 (2006).
Non-patent Literature 5: M. D. Saleh, C. Eswaran, and A. Mueen, "An automated blood vessel segmentation algorithm using histogram equalization and automatic threshold selection," J. Digit. Imag. 24, 564-572 (20011).
Non-patent Literature 6: L. Zhang, K. Lee, M. Niemeijer, R. F. Mullins, M. Sonka, and M. D. Abrmoff, "Automated segmentation of the choroid from clinical sd-oct," Invest. Ophthalmol. Vis. Sci. 53, 7510-7519 (2012).
Non-patent Literature 7: V. Kajic, M. Esmaeelpour, C. Glittenberg, M. F. Kraus, J. Honegger, R. Othara, S. Binder, J. G. Fujimoto, and W. Drexler, "Automated three-dimensional choroidal vessel segmentation of 3d 1060 nm oct retinal data," Biomed. Opt. Express 4, 134-150 (2013).
Non-patent Literature 8: N. Otsu, "A threshold selection method from gray-level histograms," Systems, Man and Cybernetics, IEEE Transactions on 9, 62-66 (1979).

SUMMARY OF THE INVENTION

Problems to be Solved by the Invention

Currently in ophthalmological care, ICGA is widely used as a visualized examination of the blood vessels at the back of the eye. This examination is indispensable in confirming the diagnosis of diseases affecting the back of the eye, but it also presents a problem in that only en-face images based on the staining density are provided and resolution is not good in the depth direction.

In essence, image signals obtained in different layers in the depth direction are overlapped, and particularly in areas of higher capillary density, the outlines of blood vessels become unclear. In addition, ICGA is an invasive examination that introduces dyes into the patient's body, so not only is the patient's body stressed, but the risk of side effects is a problem.

On the other hand, the OCT that provides the basis of the present invention is a non-invasive technology to visualize the structure at the back of the eye; however, the following problems occur in the image-processing process for obtaining OCT images of the choroidal vessels:
(1) The retinal vessels present closer to the surface than the choroidal layer become shadows that are projected into the image of the choroidal vessels, and consequently the image shows pseudo vessels that are mistaken as the choroidal vessels.
(2) While only the choroidal layer must be captured in order to obtain images of the choroidal vessels, the OCT tomographic image does not show clear boundaries between the choroidal layer and the sclerotic coat positioned deeper than the choroidal layer, and consequently the image shows pseudo vessels that are part of the sclerotic coat present near the boundaries and mistaken as the choroidal vessels.

(3) In the imaging process of OCT-measured data where each picture element (pixel) constituting the image is binarized in black and white, regions where multiple pixels of the same binary data (1 or 0) are present at higher density, for example, may be seen as the choroidal vessels, even when they are actually not, and consequently the image shows pseudo vessels.

It should be noted that, although the methods described in Non-patent Literatures 1 to 7 above certainly present good results according to what is written in the literatures, their mathematical models and separation programs are relatively complex.

An object of the present invention is to allow image information of the back of the eye close to what is obtained through angiography—information which is essential to ophthalmological diagnosis but which could heretofore be obtained only invasively—in a non-invasive manner, and also to realize an optical coherence tomography apparatus that improves the correctness of ophthalmological diagnosis by obtaining from OCT-measured data those images showing only the choroidal vessels present inside the choroidal layer, thereby accurately obtaining and quantitatively evaluating the thickness of the choroidal vessels, thickness of the vascular network, and other morphological details, as well as an image-processing program and image-processing method therefor.

Means for Solving the Problems

To achieve the aforementioned object, the present invention provides an optical coherence tomography apparatus for selectively visualizing and analyzing the vascular network in the choroidal layer comprising an optical coherence tomography, and a computer that obtains three-dimensional OCT tomographic images based on OCT-measured data acquired by the optical coherence tomography and processes the three-dimensional OCT tomographic images, wherein such optical coherence tomography apparatus for selectively visualizing and analyzing the vascular network in the choroidal layer is characterized in that: the computer functions as a means for selectively separating out only the images of the choroidal vessels from the three-dimensional OCT tomographic images to obtain image data of the choroidal vessels, and also as a means for obtaining the data to be used in the quantitative evaluation of the shape of the choroidal vessels based on the image data of the choroidal vessels; and the means for acquiring image data of the choroidal vessels is constituted in such a way that tomographic image data of the choroidal layer is extracted from OCT-measured data, the tomographic image data of the choroidal layer is sliced at equally pitched positions in the depth direction of the choroidal layer and data of image slices is extracted, after which image data of the choroidal vessels is obtained from the data of image slices.

Desirably the means for acquiring image data of the choroidal vessels is constituted in such a way that, for each of multiple windows of different sizes, each pixel in the image slice is binarized according to whether or not the pixel color density is equal to or higher than the pre-determined specified threshold in order to obtain an estimated vessel parts-extracted binary image, and in this estimated vessel parts-extracted binary image, those regions where the ratio of pixels with different binary data to each pixel in the applicable window is equal to or greater than the pre-determined specified value are deleted as pseudo vessels, while the estimated vessel parts whose diameter is smaller than the pre-determined specified diameter with respect to the dimension of the applicable window are also deleted as noise and non-vessels, in order to obtain binary image data of the vascular network in the choroidal layer.

Desirably the means for acquiring image data of the choroidal vessels is constituted in such a way that the depth-direction slope of the anterior region of Bruch's membrane at the back of the eye is detected from the three-dimensional OCT tomographic images to obtain data at the positions of the inner segment/outer segment junctions with the photoreceptor cells at the back of the eye, so that the data at the positions of the inner segment/outer segment junctions and Bruch's membrane is used to extract highly reflective structures around the retinal pigment epithelium, after which the optical intensities at the highly reflective structures are averaged to obtain image data specifying the shadows created by the retinal vessels at the highly reflective structures, which is then followed by flange-filtering the image data to emphasize the lines and binarizing the obtained image data, in order to obtain binary image data of the shadows of the retinal vessels.

Desirably the means for acquiring image data of the choroidal vessels is constituted in such a way that, for all pixels corresponding to the vessels, classified data of medium and small vessels and large vessels that have been classified by magnitude of optical intensity is created based on the tomographic image data of the choroidal layer, and based on this classified data, the binary image data of the vascular network in the choroidal layer as obtained for each of the multiple windows of different sizes is selectively combined, while at the same time binary image data of the choroidal network vessels separating out only the choroidal vessels is formed based on the binary image data of the shadows of the retinal vessels.

Desirably the means for obtaining the data to be used in the quantitative evaluation of the shape of the choroidal vessels is constituted in such a way that, based on the binary image data of the choroidal network vessels separating out only the choroidal vessels, the diameters of the choroidal vessels are estimated and diameter distribution data of the choroidal vessels is created based on the estimated data, while at the same time the thickness of the vascular network in the choroidal layer is measured and a thickness map of the vascular network in the choroidal layer is created based on the measured data.

To achieve the aforementioned object, the present invention provides a computer-installed image-processing program for an optical coherence tomography apparatus for selectively visualizing and analyzing the vascular network in the choroidal layer, where the optical coherence tomography apparatus comprises an optical coherence tomography device, and a computer that obtains three-dimensional OCT tomographic images based on OCT-measured data acquired by optical coherence tomography and processes the three-dimensional OCT tomographic images, wherein such computer-installed image-processing program for the optical coherence tomography apparatus for selectively visualizing and analyzing the vascular network in the choroidal layer is characterized in that: the computer is caused to function as a means for selectively separating out only the images of the choroidal vessels from the three-dimensional OCT tomographic images to obtain image data of the choroidal vessels, and also as a means for obtaining the data to be used in the quantitative evaluation of the shape of the choroidal vessels based on the image data of the choroidal vessels; and the means for acquiring image data of the choroidal vessels is constituted in such a way that tomographic image data of the choroidal layer is extracted from OCT-measured data, the tomographic image data of the choroidal layer is sliced at equally pitched positions in the depth direction of the choroidal layer and data of image slices is extracted, after which image data of the choroidal vessels is obtained from the data of image slices.

Desirably due to the image-processing program, the means for acquiring image data of the choroidal vessels is such that, for each of multiple windows of different sizes, each pixel in the image slice is binarized according to whether or not the pixel color density is equal to or higher than the pre-determined specified threshold in order to obtain an estimated vessel parts-extracted binary image, and in this estimated vessel parts-extracted binary image, those regions where the ratio of pixels with different binary data to each pixel in the applicable window is equal to or greater than the pre-determined specified value are deleted as pseudo vessels, while the estimated vessel parts whose diameter is smaller than the pre-determined specified diameter with respect to the dimension of the applicable window are also deleted as noise and non-vessels, in order to obtain binary image data of the vascular network in the choroidal layer.

Desirably due to the image-processing program, the means for acquiring image data of the choroidal vessels is such that the depth-direction slope of the anterior region of Bruch's membrane at the back of the eye is detected from the three-dimensional OCT tomographic images to obtain data at the positions of the inner segment/outer segment junctions with the photoreceptor cells at the back of the eye, so that the data at the positions of the inner segment/outer segment junctions and Bruch's membrane is used to extract highly reflective structures around the retinal pigment epithelium, after which the optical intensities at the highly reflective structures are averaged to obtain image data specifying the shadows created by the retinal vessels at the highly reflective structures, which is then followed by flange-filtering the image data to emphasize the lines and binarizing the obtained image data, in order to obtain binary image data of the shadows of the retinal vessels.

Desirably due to the image-processing program, the means for acquiring image data of the choroidal vessels is such that, for all pixels corresponding to the vessels, classified data of medium and small vessels and large vessels that have been classified by magnitude of optical intensity is created based on the tomographic image data of the choroidal layer, and based on this classified data, the binary image data of the vascular network in the choroidal layer as obtained for each of the multiple windows of different sizes is selectively combined, while at the same time binary image data of the choroidal network vessels separating out only the choroidal vessels is formed based on the binary image data of the shadows of the retinal vessels.

Desirably due to the image-processing program, the means for obtaining the data to be used in the quantitative evaluation of the shape of the choroidal vessels is such that, based on the binary image data of the choroidal network vessels separating out only the choroidal vessels, the diameters of the choroidal vessels are estimated and diameter distribution data of the choroidal vessels is created based on the estimated data, while at the same time the thickness of the vascular network in the choroidal layer is measured and a thickness map of the vascular network in the choroidal layer is created based on the measured data.

To achieve the aforementioned object, the present invention provides an image-processing method for an optical coherence tomography apparatus for selectively visualizing and analyzing the vascular network in the choroidal layer, where the optical coherence tomography apparatus comprises an optical coherence tomography, and a computer that obtains three-dimensional OCT tomographic images based on OCT-measured data acquired by the optical coherence tomography and processes the three-dimensional OCT tomographic images, wherein such image-processing method for the optical coherence tomography apparatus for selectively visualizing and analyzing the vascular network in the choroidal layer is characterized in that: it is a method to use the computer to selectively separate out only the images of the choroidal vessels from the three-dimensional OCT tomographic images to obtain image data of the choroidal vessels so as to obtain the data to be used in the quantitative evaluation of the shape of the choroidal vessels based on the image data of the choroidal vessels, where, to acquire the image data of the choroidal vessels, tomographic image data of the choroidal layer is extracted from OCT-measured data, the tomographic image data of the choroidal layer is sliced at equally pitched positions in the depth direction of the choroidal layer and data of image slices is extracted, after which image data of the choroidal vessels is obtained from the data of image slices.

Desirably the method for acquiring image data of the choroidal vessels is such that, for each of multiple windows of different sizes, each pixel in the image slice is binarized according to whether or not the pixel color density is equal to or higher than the pre-determined specified threshold in order to obtain an the estimated vessel parts-extracted binary image, and in this the estimated vessel parts-extracted binary image, those regions where the ratio of pixels with different binary data to each pixel in the applicable window is equal to or greater than the pre-determined specified value are deleted as pseudo vessels, while the estimated vessel parts whose diameter is smaller than the pre-determined specified diameter with respect to the dimension of the applicable window are also deleted as noise and non-vessels, in order to obtain binary image data of the vascular network in the choroidal layer.

Desirably the method for acquiring image data of the choroidal vessels is such that the depth-direction slope of the anterior region of Bruch's membrane at the back of the eye is detected from the three-dimensional OCT tomographic images to obtain data at the positions of the inner segment/outer segment junctions with the photoreceptor cells at the back of the eye, so that the data at the positions of the inner segment/outer segment junctions and Bruch's membrane is used to extract highly reflective structures around the retinal pigment epithelium, after which the optical intensities at the highly reflective structures are averaged to obtain image data specifying the shadows created by the retinal vessels at the highly reflective structures, which is then followed by flange-filtering the image data to emphasize the lines and binarizing the obtained image data, in order to obtain binary image data of the shadows of the retinal vessels.

Desirably the method for acquiring image data of the choroidal vessels is such that, for all pixels corresponding to the vessels, classified data of medium and small vessels and large vessels that have been classified by magnitude of optical intensity is created based on the tomographic image data of the choroidal layer, and based on this classified data, the binary image data of the vascular network in the choroidal layer as obtained for each of the multiple windows of different sizes is selectively combined, while at the same time binary image data of the choroidal network vessels separating out only the choroidal vessels is formed based on the binary image data of the shadows of the retinal vessels.

Desirably the method for obtaining the data to be used in the quantitative evaluation of the shape of the choroidal vessels is such that, based on the binary image data of the choroidal network vessels separating out only the choroidal vessels, the diameters of the choroidal vessels are estimated and diameter distribution data of the choroidal vessels is created based on the estimated data, while at the same time the thickness of the vascular network in the choroidal layer is measured and a thickness map of the vascular network in the choroidal layer is created based on the measured data.

Effects of the Invention

According to the optical coherence tomography apparatus with a function to visualize the vessels at the back of the eye, as well as an image-processing program and image-processing method therefor, all of which pertain to the present invention, the following effects are produced:
(1) Image information of the back of the eye close to what is obtained through angiography—information which is essential to ophthalmological diagnosis but which could heretofore be obtained only invasively—can be obtained in a non-invasive manner.
(2) By analyzing images obtained by an OCT apparatus without Doppler function, images whose contrast is similar to or higher than the contrast of simulated angiographic images of the back of the eye available through an OCT with Doppler function (Doppler OCT) can be obtained from these normal OCT images that are not Doppler-enhanced.
(3) Quantitative evaluation of the vascular system at the back of the eye, etc., becomes possible by utilizing data obtained by image-processing those images that in turn are obtained by a normal OCT apparatus without Doppler function. It should be noted that, by applying the present invention to Doppler OCT images, simulated angiographic images of the back of the eye having even higher contrast can be obtained.

BRIEF DESCRIPTION OF THE DRAWINGS

FIG. 1 Diagram showing the overall constitution of an example of the optical coherence tomography apparatus pertaining to the present invention.

FIG. 2 Diagram showing the computer that processes images in the optical coherence tomography apparatus in the above example.

FIG. 3 Diagram showing the flow of the image-processing program installed in the optical coherence tomography apparatus in the above example.

FIG. 4 Photographs showing tomographic images acquired by the optical coherence tomography apparatus in the above example.

FIG. 5(a) is a photograph showing a slice of a tomographic image obtained by the optical coherence tomography apparatus in the above example, and (b) is a black-and-white image showing a binarized version of (a).

FIG. 6(a) is an image slice of the retina obtained by the optical coherence tomography apparatus in the above example, (b) is a black-and-white image showing a binarized version of (a), and (c) is an image-processed version of (b) to emphasize the retinal vessels.

FIG. 7(a) to (d) are en-face images showing the vessel diameter distributions at 25 μm, 100 μm, 175 μm and 250 μm inward of the retinal pigment epithelium in the depth direction, respectively.

FIG. 8 Diagram explaining the conventional basic OCT.

MODE FOR CARRYING OUT THE INVENTION

A mode for carrying out the optical coherence tomography apparatus for selectively visualizing and analyzing the vascular network in the choroidal layer, as well as an image-processing program and image-processing method therefor, all of which pertain to the present invention, is explained below based on an example and by referring to the drawings.

Example

An optical coherence tomography apparatus 1 pertaining to the present invention has, as shown in FIG. 1, an optical coherence tomography device 2, and a computer 17 that image-processes OCT-measured data acquired by the optical coherence tomography device.

The optical coherence tomography (OCT) device 2 may be of any type so long as it can acquire OCT-measured data for obtaining three-dimensional OCT tomographic images; in this example, however, a swept source optical coherence tomography (SS-OCT) device is used as the optical coherence tomography device. An overview of this SS-OCT device 2 is explained first.

In FIG. 1, the light output from a wavelength-scanning light source 3 is transmitted to a fiber coupler 5 through a fiber 4. This output light is split, at the fiber coupler 5, into the object light to be irradiated onto a measuring target 7 through a fiber 6 on one hand, and the reference light to be irradiated onto a fixed reference mirror 9 through a fiber 8 on the other.

The object light is irradiated onto and reflected by the measuring target via the fiber 6, a lens 10, variable-angle scanning mirror 11 and lens 12, and returns to the fiber coupler 5 along the same route. The reference light is irradiated onto and reflected by the fixed reference mirror 9 via the fiber 8, a lens 13 and lens 14, and returns to the fiber coupler 5 along the same route.

Then, these object light and reference light are superimposed onto each other at the fiber coupler 5 and transmitted to a photodetector 16 (a PD (photodiode) or other point sensor is used for this) through a fiber 15, whereupon they are detected as spectral interference signals and these spectral interference signals are captured into a computer 17 as OCT-measured data.

At the computer 17, three-dimensional OCT tomographic images covering the depth direction (A direction) of the measuring target 7, as well as the B direction and the C direction representing the scanning directions of the scanning mirror, are formed. A display 18 is connected to the computer 17.

The wavelength-scanning light source 3 is a light source whose wavelength is varied along the temporal axis during scan, or in other words a light source whose wavelength is dependent on time. Because of this, the fixed reference mirror 9 need not be scanned (moved in the direction of optical axis to be scanned in the direction of optical axis) in order to perform A-scan (scanning in the depth direction of the measuring target; an A line is obtained as a result of this scan), and still a reflectance distribution in the depth direction of the measuring target 7 can be obtained to acquire the structure in the depth direction.

Accordingly, OCT-measured data for obtaining three-dimensional OCT tomographic images can be acquired only with B-scan (scanning in the primary direction crossing at right angles with the direction of optical axis) and C-scan (scanning in the secondary direction crossing at right angles with the direction of optical axis).

Then, based on the OCT-measured data which is detection output from the photodetector 16, three-dimensional OCT tomographic images are formed by the computer 17 and displayed on the display 18 connected to the computer 17.

The image-processing program pertaining to the present invention relates to an image-processing program which is installed in the computer constituting the optical coherence tomography apparatus and which causes the computer to function as a means for image-processing OCT-measured data that has been acquired with the optical coherence tomography device and then accurately acquiring the thickness of the choroidal vessels, thickness of the vascular network and other morphological details.

(Image-Processing Means, Image-Processing Program, Image-Processing Method)

The constitution of the image-processing means for using the computer 17 to image-process OCT-measured data that has been obtained by the optical coherence tomography, and the image-processing program installed in the computer 17 and image-processing method pertaining to the present invention, are explained below.

OCT-measured data obtained by the optical coherence tomography device of the aforementioned constitution is input to the computer 17 used as an image-processing device. This computer 17 is a normal computer and, as shown in FIG. 2, has an input part 21, output part 22, CPU 23, memory 24 and data bus 25. The image-processing program pertaining to the present invention is stored and installed in the memory 24 of the computer 17.

Based on the OCT-measured data that has been measured by the optical coherence tomography device and input to the computer 17, the image-processing program pertaining to the present invention causes the computer 17 to function as a means for forming OCT tomographic images and processing these OCT tomographic images to selectively separate out only the images of the choroidal vessels to acquire image data of the choroidal vessels, as well as a means for obtaining the data to be used in the quantitative evaluation of the shape of the choroidal vessels based on the image data of the choroidal vessels (means for accurately acquiring the thickness of the choroidal vessels, thickness of the vascular network and other morphological details), as shown by in the flow of FIG. 3.

As for the means and methods for selectively separating out only the images of the choroidal vessels to acquire image data of the choroidal vessels, the respective functions under (1) to (9) of the choroidal vessel separation process as shown in the flow of FIG. 3, and respective methods (respective steps comprising the image-processing method under the present invention), are implemented; to be specific, the means and methods explained in (1) to (9) below (respective steps comprising the image-processing method under the present invention) are included.

Also, as for the means and methods for obtaining the data to be used in the quantitative evaluation of the shape of the choroidal vessels based on the image data of the choroidal vessels, the respective functions under (10) to (13) of the choroidal vessel quantitative evaluation data creation process as shown in the flow of FIG. 3, and respective methods (respective steps comprising the image-processing method under the present invention), are implemented; to be specific, the means and methods explained in (10) to (13) below (respective steps comprising the image-processing method under the present invention) are included.

The means and image-processing methods by which the computer functions through the image-processing program to image-process OCT tomographic images, are explained below one by one according to the flow of FIG. 3:

(1) Means and Method for Extracting Image Data with Respect to Tomographic Images of the Choroidal Layer ((1) in FIG. 3)

While three-dimensional tomographic images of the back of the eye, which is the measuring target, are obtained from OCT-measured data, the image-processing program causes the computer to function in such a way that it extracts the image data with respect to, among these three-dimensional tomographic images, tomographic images that roughly correspond to the region of the choroidal layer.

To extract the region of the choroidal layer as mentioned above, Bruch's membrane (structure that isolates the choroidal layer and the retinal pigment epithelium) is detected and automatically cut and discarded. This discarding is carried out in such a way that square signal intensities are calculated along the A-line of the choroidal layer and Bruch's membrane in the depth direction from the retinal pigment epithelium and from the front toward the rear, and the pigments at which the slope of square signal intensities becomes the minimum are certified as those of Bruch's membrane, and Bruch's membrane is automatically deleted.

(2) Means and Method for Extracting Multiple Image Data of a Three-Dimensional Tomographic Image of the Choroidal Layer Sliced at Equally Pitched Depth Positions ((2) in FIG. 3)

The image-processing program causes the computer to function in such a way that a three-dimensional tomographic image of the choroidal layer is sliced (or more specifically cut to thin sections at right angles to the depth direction) at multiple equally pitched depth positions in the depth direction of the choroidal layer from the retinal pigment epithelium, to extract two-dimensional images (en-face images) as viewed from the front side of the eye at each depth position.

It should be noted that, for the region of the choroidal layer whose tomographic image has been sliced, the region to the depth of 370 μm, for example, from Bruch's membrane positioned between the retinal pigment epithelium and choroidal layer is selected, and this region partially includes the sclerotic coat at the back of the choroidal layer.

In other words, the region immediately below Bruch's membrane and amply including the choroidal layer (such as to 370 μm) is selected and flattened (sliced as a thin flat surface) as the analysis region. Here, since the volume is selected by considering the typical maximum thickness of the choroidal layer around the macular spot, in most cases the region includes all of the choroidal layer and some of the sclerotic coat.

Also, an appropriate averaging filter (20×20 pixels: 58.6 μm in the horizontal direction, 58.6 μm in the depth direction, etc.) is applied to lessen the speckles and thereby improve the image quality.

FIG. 4 (a) to (d) show extracted image slices corresponding to different positions in the depth direction of the choroidal layer (slices containing 20×20 pixels within their horizontal plane, having an area of a 58.6-μm square, and thickness of 58.6 μm), where the depth from the retinal pigment epithelium is 25 μm in (a), 100 μm in (b), 175 μm in (c), and 250 μm in (d).

Next, the image-processing program causes the computer to function in such a way that, for the data of multiple image slices obtained in (2) above, the means and methods under (3), (4) and (5) below are performed one by one with respect to the 47-µm window (window consisting of a 47-µm square), 94-µm window (window consisting of a 94-µm square), 188-µm window (window consisting of a 188-µm square), and 375-µm window (window consisting of a 375-µm square), respectively.

(3) Means and Method for Extracting Estimated Vessel Parts to Form a Binary Image ((3) in FIG. 3)

The image-processing program causes the computer to function in such a way that estimated vessel parts are extracted for the data of multiple image slices obtained in (2) above. Here, estimated vessel parts are "parts that can be roughly estimated as the choroidal vessels" and include, in reality, parts other than the vessels, shadows, and other non-vessel parts.

Under the means and method for extracting estimated vessel parts to form a binary image, the color density difference between the image data of vessels and non-vessels is given attention and each of the multiple pixels included in the windows is binarized in such a way that "1" is assigned if the color density is equal to or higher than a pre-determined specified threshold, or "0" is assigned if the color density is lower than the threshold.

Then, black is assigned to the pixels of "1" as estimated vessel parts, while white is assigned to the pixels of "0" as non-vessel parts, to form a black-and-white binary image. This operation is repeated for the entire range of the image data of one slice, by shifting the windows, respectively, to form a black-and-white binary image covering for the entire range of the image data of one slice.

FIG. 5 (a) shows one example of image slice, and by binarizing each pixel therein according to the means and method for extracting estimated vessel parts to form a binary image, the black-and-white binary image as shown in FIG. 5 (b) can be obtained.

The above means and method is explained in greater detail below. An en-face image is divided into parts and the resulting windows (regions) are binarized using the threshold (referred to as "adaptive threshold") determined by the formula (Mathematical Formula 1) below.

$$p(x_0, y_0) \equiv \sum_{x_i, y_i} I(x_i, y_i) g(x_i, y_i) \Big/ \sum_{x_i} \sum_{y_i} g(x_i, y_i)$$ [Mathematical Formula 1]

Here, $x_0$ and $x_1$ are lateral coordinates, while $y_0$ and $y_1$ are vertical coordinates. Sum $\Sigma$ is performed on the pixels inside the window (region) whose center is $(x_0, y_0)$ (such as $w_x$ µm×$w_y$ µm etc.). $I(x_i, y_i)$ is a log of OCT image intensity, while $g(x_i, y_i)$ represents the so-called edge intensity defined by the formula (Mathematical Formula 2) below.

$$g(x_i, y_i) \equiv \sqrt{\left(\frac{\partial I(x_i, y_i)}{\partial x_i}\right)^2 + \left(\frac{\partial I(x_i, y_i)}{\partial y_i}\right)^2}$$ [Mathematical Formula 2]

Such filter (adoptive filter) gives a binary image of "1" pixels representing vessel regions and "0" pixels representing non-vessel regions. Such means and method under the present invention allows for binarization of gray scale images at high speed based on a simple procedure.

(4) Means and Method for Deleting Pseudo Vessels Using a Busyness Filter ((4) in FIG. 3)

While the means and method for extracting estimated vessel parts to form a binary image in (3) above gives a black-and-white binary image like the one shown in FIG. 5 (b), this binary image inevitably includes non-vessel parts that are simply background, not vessels, but identified as vessels (referred to as "pseudo vessels").

In such a case, proper binarization is not possible if the window (region) only consists of background and includes no vessels, and consequently the background is also classified as vessels. In this case, what look like assemblies of fine edges are seen, instead of continuous vessels. The image-processing program pertaining to the present invention causes the computer to function as a means for deleting such pseudo vessels using a busyness filter.

The principle of how vessels and pseudo vessels are identified using a busyness filter is explained below. Assume that, with respect to "one given pixel A" (whose binary data is "0," for example) in a window, "pixel B with different binary data (whose binary data is "1," for example) exists in the window, in which case "given pixel A" above is defined as an edge pixel.

Estimated vessel parts in regions where such edge pixels account for 20% or more, are deleted as pseudo vessels. The ratio of edge pixels is called "busyness value." To be specific, the busyness value representing the ratio of edge pixels is acquired for the entire regions of the black-and-white binary image like the one shown in FIG. 5 (b), by shifting the windows.

If the binary data of the pixels in true vessel parts is assigned "1" and black in the binary image, while the binary data of the pixels in non-vessel parts is assigned "0" and white in the binary image, the busyness value becomes higher in the non-vessel regions.

Those regions where this busyness value is 20% or more are deleted as pseudo vessels. On the binary image (not illustrated here) from which pseudo vessels have been deleted, the pseudo vessel parts in the region on the right side of FIG. 5 (b) around the middle height, for example, are deleted.

To explain more clearly, the busyness filter focuses on a specific pixel on the binary image and uses the eight pixels around it to define whether or not the region is busy. The region is not busy if all peripheral pixels have the same value as the specific pixel; on the other hand, the region is busy if at least one pixel has a value different from the specific pixel.

In the same window (region) as the window (region) used in the aforementioned adaptive filter, the busyness value (busyness) is defined by the ratio of the number of busy pixels (referred to as "edge pixels") to the total number of pixels in this window (region). In general, the busyness value is higher with random images, and lower with images having clearly identifiable windows (regions).

For example, if the window (region) size $w_x \times w_y$ is 375 µm, any window (region) whose busyness value is 0.2 or greater is considered a window (region) not containing vessels and "0" indicating a non-vessel region is set.

(5) Means and Method for Erasing Non-Vessel Pixels ((5) in FIG. 3)

If the window size is significantly greater than the vessel diameter, parts of vessels where the contrast changes hinder the identification of vessels and non-vessels.

To be specific, sufficient contrast cannot be obtained if the window (region) w size is much greater than the vessel diameter, and consequently vessel structures cannot be detected well (empirically when the vessels are smaller than one-fifth the window size, for example, as described later). In other words, small vessels (smaller than one-fifth the window size) that have been detected are artifact (false images or noise) and must be erased.

For this reason, the image-processing program under the present invention causes the computer to function as a means for further erasing the pixels constituting the non-vessel parts, from the binary image obtained in (4) above. The details of this function are explained below.

First, the binary image obtained in (4) above is reversed. In other words, the pixels representing the vessels that have been assigned "1" and black are changed to "0" and white, while the pixels representing the non-vessel parts that have been assigned "0" and white are changed to "1" and black.

Additionally, particle parts whose diameter is smaller than two pixels are erased. The purpose of this operation is to fill small holes in large vessels. This pre-processing is performed because without it, the aforementioned particle parts will be identified as two adjoining thin vessels in the morphological analysis explained next.

Morphological analysis is performed after the aforementioned pre-processing. The inventors of the present invention gained the knowledge, during the course of research and development of the present invention, that the means and method for erasing pseudo vessels using a busyness filter as described in (4) above could not identify vessels whose diameter is smaller than the window size (diameter smaller than the pre-determined specified diameter corresponding to the window size, or specifically diameter smaller than one-fifth the window size).

In other words, estimated vessel parts whose diameter is smaller than one-fifth the window size are to be erased as noise and non-vessels. Based on this knowledge, estimated vessel parts whose diameter is smaller than one-fifth the window size are erased as noise and non-vessels as the first step of morphological analysis.

As the next step of morphological analysis, the Heywood circularity factor ("Length of the outer periphery of a given shape"/"Length of the circumference") is used to erase those pixels constituting circular or near-circular shapes that are different from the shapes of vessels. This Heywood circularity factor itself is known and defined as "Length of the outer periphery of a given shape"/"Length of the circumference."

To be specific, pixels constituting those parts whose Heywood circularity factor is less than 1.5 are erased. If this factor is less than 1.5, the shape is recognized as a circular or near-circular and not a long thin vessel, but if it is 1.5 or greater, the shape is recognized as long and thin, or specifically as that of a vessel. In this way, pixels constituting non-vessel parts are erased.

When the foregoing is organized, first the binary image is reversed (vessel regions="0," other regions="1"). Then, the regions of "1" smaller than two pixels are eliminated (set to "0"). This is to eliminate small holes (noise) in large vessels.

Next, the circular structures to be eliminated (such as diameter w/5) are convoluted to widen (dilate) the regions having the value "1." Next, the regions are reduced (eroded) to eliminate the small structures while maintaining the large structures.

(6) Means and Method for Separating Out the Highly Reflective Structures Around the Retinal Pigment Epithelium ((6) in FIG. 3)

On the OCT tomographic image of the choroidal layer, shadows of the retinal vessels in front are projected and mistaken as the choroidal vessels. This mistake can inhibit accurate quantitative evaluation of the thickness of the choroidal layer and thickness of the choroidal vessels. Accordingly, these shadows must be removed.

As the first step to solve this problem, the image-processing program pertaining to the present invention causes the computer to function as a means for separating out the highly reflective structures around the retinal pigment epithelium. According to such means and method, the following operation is performed concurrently with the operation to extract the choroidal layer in (1) above, as shown in the flow of FIG. 3.

In other words, the inner segment/outer segment junctions (IS/OS lines) of the regional pigment epithelium and photoreceptor cells (optical receptors) represent highly reflective structures of high reflectance, and the retinal vessels are positioned at these inner segment/outer segment junctions. Accordingly, projected images of the retinal vessels are most clearly seen at these inner segment/outer segment junctions that are highly reflective structures.

For this reason, images of the retinal vessels as projected on the highly reflective structures can be extracted from the position of maximum positive optical intensity slope on the OCT tomographic image. To be specific, the depth-direction slope (degree of change) in the anterior region of Bruch's membrane is measured to detect the position of maximum positive optical intensity slope, thereby obtaining data at the positions of the inner segment/outer segment junctions of the retinal pigment epithelium and photoreceptor cells (optical receptors).

Then, by using this data at the positions of the inner segment/outer segment junctions and Bruch's membrane, highly reflective structures around the retinal pigment epithelium can be separated out to extract optical intensities. The optical intensities of the separated highly reflective structures are averaged to obtain an image of the highly reflective structures, as shown in FIG. 6 (a). Such data specifies the signals of the shadows of the retinal vessels as explained below.

(7) Means and Method for Separating Out the Shadows Created by the Retinal Vessels ((7) in FIG. 3)

As explained in (6) above, the retinal vessels enter the image data of the choroidal layer as shadows and are mistaken as the choroidal vessels in the data of image slices. This mistake can inhibit accurate quantitative evaluation of the thickness of the choroidal layer and thickness of the choroidal vessels.

Accordingly, the images at the highly reflective structures obtained in (6) above must be used to separate out the shadows created by the retinal vessels, from the choroidal vessels. The image-processing program pertaining to the present invention causes the computer to function as a means for separating out the shadows created by the retinal vessels and to perform the following operations.

The image data at the highly reflective structures is flange-filtered to emphasize the lines, and as a result of non-linear binarization with appropriate threshold (flange filtering, etc.), image data is obtained which consists of "1" representing the vessel parts and "0" representing the remainder, as shown in FIG. 6 (b).

Thereafter, morphological closing (the regions having the value "1" are eroded and then dilated) is performed to ensure continuity of the vessels, which effectively removes the shadows of the retinal vessel image that have been extracted slightly thicker than they actually are, from the choroidal vessel image. Since the retinal vessel image is completely removed, the binary image data shown in FIG. 6 (c) can be obtained.

(8) Means and Method for Classifying the Pixels Based on Optical Intensity ((8) in FIG. 3)

As mentioned above, the processes in (3) to (5) above are performed on the four windows of different sizes, where, for the reason described later, the data obtained with respect to the four windows is combined in an appropriate manner to finally evaluate the thickness and diameter of the choroidal vessels, etc., quantitatively.

To combine the data obtained with respect to the four windows in an appropriate manner, pixels corresponding to large vessels and pixels corresponding to medium and small vessels are classified beforehand as follows. The image-processing program pertaining to the present invention causes the computer to function as a means for classifying the pixels in the OCT tomographic image based on the optical intensity of each pixel.

In the combination process, all pixels in the parts of the choroidal layer shown in the sectional image, as obtained in (1) above, are first classified into pixels constituting large vessels and pixels constituting medium and small vessels. Since the measurement light passes through the choroidal layer and scatters in the blood, the intensities of the OCT-obtained spectral interference signals, or specifically optical intensities on OCT tomographic images, of the thick choroidal vessels are smaller than the same optical intensities of the thin medium and small vessels present near the retinal pigment epithelium.

Based on these different optical intensities on OCT tomographic images, the pixels are classified into bright ones corresponding primarily to thin medium and small vessels, and dark ones corresponding primarily to thick vessels. In reality, this classification is performed according to the known Otsu threshold (refer to Non-patent Literature 8), where all pixels are simultaneously classified into medium and small vessels if their optical intensities on OCT tomographic images are greater than the Otsu threshold, or into large vessels if their optical intensities are smaller than the threshold, in order to create roughly classified data.

(9) Means and Method for Combining the Image-Processing Data Based on Different Windows ((9) in FIG. 3)

When dividing the entire view field (such as a 6-mm square) being observed into multiple regions, one effective means and method is to divide the view field into several regions of different scales and then extract the vessel structure from each region to combine the extracted vessel structures.

For example, if a 6-mm square field is divided into four regions of different scales including 1/128, 1/64, 1/32 and 1/16, the sizes w ($=w_x=w_y$) of these regions become 47 μm, 94 μm, 188 μm, and 375 μm, respectively.

Since vessel diameters range from several microns to several hundreds of microns, the adaptive threshold allows for extraction of vessels having most appropriate diameters for each division. Accordingly, the aforementioned means and method for combining the results of (four) scaled regions to extract vessels is effective.

This point is clarified further. Using the means and method shown in (5) above, the estimated vessel parts of diameters smaller than one-fifth the window size were erased as noise and non-vessels. However, this does not mean the true small vessels are separated out. Small windows are not appropriate for performing proper separation.

The reason is as follows. Under the means and method for extracting the estimated vessel parts and forming a binary image, each of the multiple pixels included in the window was binarized to "1" if the color density was equal to or higher than the specified threshold, or to "0" if the color density was lower than the threshold.

If the number of pixels in the true edges at the boundaries between the vessels and background is very small in the applicable window, then the means and method shown in (5) above cannot provide an appropriate threshold. This is why vessels having large diameters cannot be identified using small windows.

Since the diameters of the choroidal vessels range from several μm to several hundreds of μm, it is necessary to identify the vessels over a wide diameter range. For this reason, the present invention uses multiple windows of different sizes to perform image-processing so that the vessels can be identified over a wide diameter range on multiple scales, as mentioned above.

In this example, the windows have square sizes w of 47 μm, 94 μm, 188 μm, and 375 μm, as mentioned above, corresponding to the sizes 1/128, 1/64, 1/32 and 1/16 of a 6-mm image, respectively.

The image-processing program pertaining to the present invention causes the computer to function as a means for combining the image-processing data that has been obtained based on four windows of different sizes (means for selecting which window size the image-processing data to be used should be based on).

Under this means and method for combining the image-processing data, which window size the image-processing data V ($x_i,y_i,z_i,w$) to be used should be based on, is selected as follows. Here, binary image data is based on a window of size w ("1" for vessel pixels, or "0" for non-vessel pixels).

(a) In the case of I ($x_i,y_i,z_i$)≥k*, the image-processing data of V ($x_i,y_i,z_i,w=47$)∪V ($x_i,y_i,z_i,w=94$) can be used.

Here, I ($x_i,y_i,z_i$) represents the optical intensity (log value) of the $x_i,y_i,z_i$ pixel in an OCT tomographic image, while k* is the Otsu threshold. V ($x_i,y_i,z_i,w=47$) represents binary image data based on a window of w=47 μm. V ($x_i,y_i,z_i,w=94$) represents binary data based on a window of w=94 μm. ∪ means logical sum operation.

In essence, the binary image-processing data based on a window of size 47 μm or 94 μm is adopted according to the pixels classified as equal to or greater than the Otsu threshold k* in (8) above. This means that, for small vessels, binary image-processing data based on a small window is adopted.

(b) If I ($x_i,y_i,z_i$)≥k* is not satisfied, binary image data of V ($x_i,y_i,z_i,w=94$)∪V ($x_i,y_i,z_i,w=188$)∪V ($x_i,y_i,z_i,w=375$) can be used.

Here, V ($x_i,y_i,x_i,w=188$) represents binary image data based on a window of w=188 μm, while V ($x_i,y_i,z_i,w=375$) represents binary image data based on a window of w=375 μm. ∪ means logical sum operation.

In essence, binary image data based on a window of size 94 μm, 188 μm, or 375 μm is adopted according to the pixels classified as not equal to or greater than the Otsu threshold k* in (8) above. This means that, for large vessels, binary image data based on a large window is adopted.

As described above, the image-processing program pertaining to the present invention causes the computer to function in such a way that binary image data based on windows of different sizes is combined according to the optical intensities of the pixels on tomographic images.

It should be noted that the binary data based on the means and method for separating out the highly reflective structures around the retinal pigment epithelium in (6) above, and the means and method for separating out the shadows created by the retina vessels in (7) above, is reflected in the binary image data based on windows of different size in this process under (9).

(10) Means and Method for Estimating the Diameters of the Choroidal Vessels ((10) in FIG. 3)

The image-processing program pertaining to the present invention is caused to function as a means for estimating the diameters of the vessels in the respective parts of the black-and-white binary image based on the binary image data finally obtained in (9) above.

To be specific, the length of a vessel in the direction crossing at right angles with the length direction of the vessel gives the vessel's diameter. Through morphological opening (dilating, and then eroding, of the regions having the value "1") based on a circular pattern, those vessels having diameters greater than the pattern are extracted.

Accordingly, the vessel diameters can be classified by performing morphological opening based on a circle whose diameter is expressed by $d_1 = i \times d_1$ ($i=1 \ldots i_{max}$) where $d_1$ represents the minimum diameter to be extracted and $d_{i_{max}}$ represents the maximum diameter to be extracted.

(11) Means and Method for Creating Diameter Distribution Data of the Choroidal Vessels ((11) in FIG. 3)

The image-processing program pertaining to the present invention is caused to function as a means for creating diameter distribution data of the choroidal vessels based on the estimated diameter data of the vessels in the respective parts of the binary image obtained in (10) above.

By performing the vessel diameter classification process in (10) above on en-face images of different depths, a vessel diameter distribution like the one shown in FIG. 7 can be obtained.

FIG. 7 (a) to (d) show vessel diameter distributions of en-face images of 25 μm, 100 μm, 175 μm, and 250 μm inward from the retinal pigment epithelium (RPE) in the depth direction, respectively, where the brightness indicates the vessel diameter, and the indicator for brightness and vessel diameter size is shown at the bottom of FIG. 7. Note, however, that the regions where no choroidal vessels are present and regions of the retinal vessels appear dark because the brightness is irrelevant in these regions.

Incidentally, the means and method for obtaining a vessel diameter distribution, as mentioned above, requires a lot of time if the circular pattern is small. By performing morphological opening with the diameter of the circular pattern fixed to the maximum vessel diameter to be detected (such as $d_1 = d_f (= d_{i_{max}})$), and also with the en-face image of vessels resized to $N/i \times N/i$ (the number of pixels is decreased to reduce the image size to $1/i$th), the vessel diameters can be classified at high speed.

(12) Means and Method for Measuring the Thickness of the Vascular Network in the Choroidal Layer ((12) in FIG. 3)

The image-processing program pertaining to the present invention is caused to function as a means for measuring the thickness of the vascular network in the choroidal layer based on the estimated diameter data of the vessels in the respective parts of the binary image obtained in (10) above.

The specifics of this means and method for measuring the thickness of the vascular network in the choroidal layer are as follows. The thickness of the choroidal vascular network represents the thickness between the retinal pigment epithelium (RPE) and an envelope that smoothly connects the enveloping surfaces of the rear (back) side of the choroidal vessels (resembling the surface of a wrapping cloth covering the vascular network region).

This envelope is extracted using an active deformable surface model. First, the retinal pigment epithelium (RPE) is flattened and turned upside down, and meshed in a deformable manner from the top (back side of the back of the eye). In the explanation given here, the z coordinate (coordinate in the depth direction at the back of the eye) is positive (z) on the front side (back side of the back of the eye).

When a grid point of the mesh is considered a control point and interaction (force) is given to the control point, the surface deforms and a smooth, optimal envelope is given. This task is repeated at all control points. The interaction (force) $F_j$ is defined by the formula below.

$$F_j^{(\tau)} = \alpha F_j^{(\tau)} + \beta R_j^{(\tau)} + G$$

Here, $\tau$ represents the number of repetitions, j represents the number of the control points, G represents a negative constant (something like gravity), and a downward force is applied to the whole mesh (all control points). $R_j^{(\tau)}$ indicates local rigidity of the deformed surface, and is expressed by the formula (Mathematical Formula 3) below.

$$R_j^{(\tau)} = \left( \frac{\partial^2 S(x_i, y_i)}{\partial x_i^2} + \frac{\partial^2 S(x_i, y_i)}{\partial y_i^2} \right) \Bigg|_{x_i = u_j, y_i = v_j} \quad \text{[Mathematical Formula 2]}$$

Here, $S(x_i, y_i)$ is a smooth surface obtained by an appropriate interpolation method such as the two-dimensional bi-cubic interpolation (interpolation method whereby the height information of 4×4 (16) points around the target position is used to express the surface with a cubic function), while $(u_j, v_j)$ is the coordinate of the jth control point. $P_j^{(\tau)}$ indicates a repulsive force defined by the average vessel diameter of a local area.

The local area may have a mesh size around a control point, for example. $\alpha$ and $\beta$ are positive constants used for balancing the aforementioned three forces. The position (z coordinate) of control point is updated through repeated operations. In other words, the position of control point is indicated by the formula (Mathematical Formula 4) below.

$$z_j^{(\tau+1)} = \begin{cases} z_j^{(\tau)} - 1 & \text{for} \quad F_j^{(\tau)} < -F_\theta \\ z_j^{(\tau)} & \text{for} \quad -F_\theta \leq F_j^{(\tau)} \leq F_\theta \\ z_j^{(\tau)} + 1 & \text{for} \quad F_j^{(\tau)} > F_\theta \end{cases}$$

Here, $z_j^{(\tau)}$ indicates the position of the jth control point at the $\tau$th repetition, while $F_\theta$ is a pre-determined positive threshold. Repetition continues until all control points have stabilized (settled). Once the control points have settled, an appropriate interpolation such as the two-dimensional bi-cubic interpolation is performed on these control points to obtain an envelope of the vascular network.

(13) Means and Method for Creating a Thickness Map of the Vascular Network in the Choroidal Layer ((13) in FIG. 3)

The image-processing program pertaining to the present invention is caused to function as a means for creating a thickness map of the vascular network in the choroidal layer based on the measured thickness data of the vascular network in the choroidal layer obtained in (12) above.

The foregoing explained, based on an example, the mode for carrying out the optical coherence tomography apparatus for selectively visualizing and analyzing the vascular network in the choroidal layer, as well as an image-processing program and image-processing method therefor; however, it goes without saying that the present invention is not limited to this example in any way and that various examples may be given within the scope of the technical items described in "What Is Claimed Is."

INDUSTRIAL FIELD OF APPLICATION

By using the optical coherence tomography apparatus for selectively visualizing and analyzing the vascular network in the choroidal layer, as well as an image-processing program and image-processing method therefor, all of which pertain to the present invention, the vascular network in the choroidal layer can be separated out from other layers and non-vessels and extracted for quantitative evaluation from an OCT image obtained by a normal optical coherence tomography apparatus which is not Doppler-enhanced; accordingly, the present invention is best suited for ophthalmological diagnostic systems.

For example, the present invention is extremely useful in very early diagnosis of glaucoma, diabetic retinopathy, age-related macular degeneration, etc., through simulated angiography or quantitative evaluation of the choroidal vessels. Furthermore, it can also be applied to OCT images from Doppler-enhanced optical coherence tomography apparatuses.

DESCRIPTION OF THE SYMBOLS

1 Optical coherence tomography apparatus
2 Swept source OCT device
3 Wavelength-scanning light source
4, 6, 8, 15 Fiber
5 Fiber coupler
7 Measuring target
9 Fixed reference mirror
11 Scanning mirror
10, 12, 13, 14 Lens
16 Photodetector
17 Computer
18 Display
21 Input part
22 Output part
23 CPU
24 Memory
25 Data bus
43 OCT device
44 Light source
45 Collimator lens
46 Beam splitter
47 Objective lens in the object arm
48 Measuring target
49 Objective lens in the reference arm
50 Reference mirror
51 Focusing lens
52 Photodetector (photodiode, etc.)

What is claimed is:

1. An optical coherence tomography apparatus for selectively visualizing and analyzing a vascular network in a choroidal layer comprising:
   an optical coherence tomography device, and
   a computer that obtains three-dimensional OCT tomographic images based on OCT-measured data acquired by the optical coherence tomography device and processes the three-dimensional OCT tomographic images,
   wherein the computer comprises:
   a means for acquiring image data of the choroidal vessels by selectively separating out only images of choroidal vessels from the three-dimensional OCT tomographic images, and
   a means for obtaining data to be used in a quantitative evaluation of a shape of the choroidal vessels based on the image data of the choroidal vessels;
   wherein the means for acquiring image data of the choroidal vessels performs extracting tomographic image data of the choroidal layer from the OCT-measured data, extracting data of image slices from the tomographic image data of the choroidal layer, which data of image slices are image data representing the choroidal layer sliced at equally pitched positions in a depth direction of the choroidal layer, and then acquiring the image data of the choroidal vessels from the data of image slices, and
   wherein the means for acquiring image data of the choroidal vessels is constituted in a manner that, for each of multiple windows of different sizes, each pixel in the image slice is binarized according to whether or not a pixel color density is equal to or higher than a pre-determined specified threshold in order to obtain an estimated vessel parts-extracted binary image, and
   in this estimated vessel parts-extracted binary image, those regions where a ratio of pixels with different binary data to each pixel in an applicable window is equal to or greater than a pre-determined specified value are deleted as pseudo vessels, while the estimated vessel parts whose diameter is smaller than a pre-determined specified diameter with respect to a dimension of the applicable window are also erased as noise and non-vessels, in order to obtain binary image data of the vascular network in the choroidal layer.

2. The optical coherence tomography apparatus for selectively visualizing and analyzing a vascular network in a choroidal layer according to claim 1, wherein the means for acquiring image data of the choroidal vessels is constituted in a manner that a depth-direction slope of an anterior region of Bruch's membrane at a back of an eye is detected from the three-dimensional OCT tomographic images to obtain data at positions of inner segment/outer segment junctions with photoreceptor cells at the back of the eye, so that data at the positions of the inner segment/outer segment junctions and Bruch's membrane is used to extract highly reflective structures around a retinal pigment epithelium, after which optical intensities at the highly reflective structures are averaged to obtain image data specifying shadows created by retinal vessels at the highly reflective structures, which is then followed by flange-filtering the image data to emphasize lines and binarizing the obtained image data, in order to obtain binary image data of the shadows of the retinal vessels.

3. The optical coherence tomography apparatus for selectively visualizing and analyzing a vascular network in a choroidal layer according to claim 2, wherein the means for acquiring image data of the choroidal vessels is constituted in a manner that, for all pixels corresponding to vessel parts, classified data of medium and small vessels and large vessels that have been classified by magnitude of optical intensity is created based on the tomographic image data of the choroidal layer, and based on this classified data, the binary image data of the vascular network in the choroidal layer as obtained for each of the multiple windows of different sizes is selectively combined, while at the same time binary image data of choroidal network vessels separating out only the choroidal vessels is formed based on the binary image data of the shadows of the retinal vessels.

4. The optical coherence tomography apparatus for selectively visualizing and analyzing a vascular network in a choroidal layer according to claim 3, wherein the means for obtaining data to be used in a quantitative evaluation of a shape of the choroidal vessels is constituted in a manner that, based on the binary image data of the choroidal network vessels separating out only the choroidal vessels, diameters of the choroidal vessels are estimated and diameter distribution data of the choroidal vessels is created based on estimated data, while at a same time a thickness of the vascular network in the choroidal layer is measured and a thickness map of the vascular network in the choroidal layer is created based on measured data.

5. A computer readable non-transitory medium storing a computer-installed image-processing program for an optical coherence tomography apparatus for selectively visualizing and analyzing a vascular network in a choroidal layer, where the optical coherence tomography apparatus comprises an optical coherence tomography device, and a computer that obtains three-dimensional OCT tomographic images based on OCT-measured data acquired by the optical coherence tomography device and processes the three-dimensional OCT tomographic images,
wherein the computer is caused to perform:
a step for acquiring image data of the choroidal vessels by selectively separating out only images of choroidal vessels from the three-dimensional OCT tomographic images, and
a step for obtaining data to be used in a quantitative evaluation of a shape of the choroidal vessels based on the image data of the choroidal vessels;
wherein the step for acquiring image data of the choroidal vessels performs extracting tomographic image data of the choroidal layer from the OCT-measured data, extracting data of image slices from the tomographic image data of the choroidal layer, which data of image slices are image data representing the choroidal layer sliced at equally pitched positions in a depth direction of the choroidal layer, and then acquiring the image data of the choroidal vessels from the data of image slices,
wherein the step for acquiring image data of the choroidal vessels is such that, for each of multiple windows of different sizes, each pixel in the image slice is binarized according to whether or not a pixel color density is equal to or higher than a pre-determined specified threshold in order to obtain an estimated vessel parts-extracted binary image, and
in this estimated vessel parts-extracted binary image, those regions where a ratio of pixels with different binary data to each pixel in an applicable window is equal to or greater than a pre-determined specified value are erased as pseudo vessels, while the estimated vessel parts whose diameter is smaller than a pre-determined specified diameter with respect to a dimension of the applicable window are also erased as noise and non-vessels, in order to obtain binary image data of the vascular network in the choroidal layer.

6. The computer readable non-transitory medium storing a computer-installed image-processing program for an optical coherence tomography apparatus for selectively visualizing and analyzing a vascular network in a choroidal layer according to claim 5, wherein the step for acquiring image data of the choroidal vessels is such that a depth-direction slope of an anterior region of Bruch's membrane at a back of an eye is detected from the three-dimensional OCT tomographic images to obtain data at positions of inner segment/outer segment junctions with photoreceptor cells at the back of the eye, so that data at the positions of the inner segment/outer segment junctions and Bruch's membrane is used to extract highly reflective structures around a retinal pigment epithelium, after which optical intensities at the highly reflective structures are averaged to obtain image data specifying shadows created by retinal vessels at the highly reflective structures, which is then followed by flange-filtering the image data to emphasize lines and binarizing the obtained image data, in order to obtain binary image data of the shadows of the retinal vessels.

7. The computer readable non-transitory medium storing a computer-installed image-processing program for an optical coherence tomography apparatus for selectively visualizing and analyzing a vascular network in a choroidal layer according to claim 6, wherein the step for acquiring image data of the choroidal vessels is such that, for all pixels corresponding to vessels parts, classified data of medium and small vessels and large vessels that have been classified by magnitude of optical intensity is created based on the tomographic image data of the choroidal layer, and based on this classified data, the binary image data of the vascular network in the choroidal layer as obtained for each of the multiple windows of different sizes is selectively combined, while at a same time binary image data of choroidal network vessels separating out only the choroidal vessels is formed based on the binary image data of the shadows of the retinal vessels.

8. The computer readable non-transitory medium storing a computer-installed image-processing program for an optical coherence tomography apparatus for selectively visualizing and analyzing a vascular network in a choroidal layer according to claim 7, wherein the step for obtaining data to be used in a quantitative evaluation of a shape of the choroidal vessels is such that, based on the binary image data of the choroidal network vessels separating out only the choroidal vessels, diameters of the choroidal vessels are estimated and diameter distribution data of the choroidal vessels is created based on estimated data, while at a same time a thickness of the vascular network in the choroidal layer is measured and a thickness map of the vascular network in the choroidal layer is created based on measured data.

9. An image-processing method for an optical coherence tomography apparatus for selectively visualizing and analyzing a vascular network in a choroidal layer, where the optical coherence tomography apparatus comprises:
an optical coherence tomography device, and
a computer that obtains three-dimensional OCT tomographic images based on OCT-measured data acquired by the optical coherence tomography device and processes the three-dimensional OCT tomographic images,
wherein the method, by using the computer, selectively separates out only images of choroidal vessels from the three-dimensional OCT tomographic images to acquire image data of the choroidal vessels so as to obtain data to be used in a quantitative evaluation of a shape of the choroidal vessels based on the image data of the choroidal vessels, where a step for acquiring the image data of the choroidal vessels comprises extracting tomographic image data of the choroidal layer from the OCT-measured data, extracting data of image slices from the tomographic image data of the choroidal layer, which data of image slices are image data representing the choroidal layer sliced at equally pitched positions in a depth direction of the choroidal layer and data of image slices is, and then acquiring the image data of the choroidal vessels from the data of image slices, wherein the step for acquiring image data of the choroidal vessels is such that, for each of multiple windows of different sizes, each pixel in the image slice is binarized according to whether or not a pixel color density is equal to or higher than a pre-determined specified threshold in order to obtain an estimated vessel parts-extracted binary image, and in this estimated vessel parts-extracted binary image, those regions where a ratio of pixels with different binary data to each pixel in an applicable window is equal to or greater than a pre-determined specified value are deleted as pseudo vessels, while the estimated vessel parts whose diameter is smaller than a pre-determined specified diameter with respect to a dimension of the applicable window are also deleted as noise and non-vessels, in order to obtain binary image data of the vascular network in the choroidal layer.

10. The image-processing method for an optical coherence tomography apparatus for selectively visualizing and analyzing a vascular network in a choroidal layer according to claim 9, wherein the method for acquiring image data of the choroidal vessels is such that a depth-direction slope of an anterior region of Bruch's membrane at a back of an eye is detected from the three-dimensional OCT tomographic images to obtain data at positions of inner segment/outer segment junctions with photoreceptor cells at the back of the eye, so that data at the positions of the inner segment/outer segment junctions and Bruch's membrane is used to extract highly reflective structures around a retinal pigment epithelium, after which optical intensities at the highly reflective structures are averaged to obtain image data specifying shadows created by retinal vessels at the highly reflective structures, which is then followed by flange-filtering the image data to emphasize lines and binarizing the obtained image data, in order to obtain binary image data of the shadows of the retinal vessels.

11. The image-processing method for an optical coherence tomography apparatus for selectively visualizing and analyzing a vascular network in a choroidal layer according to claim 10, wherein the method for acquiring image data of the choroidal vessels is such that, for all pixels corresponding to vessels parts, classified data of medium and small vessels and large vessels that have been classified by magnitude of optical intensity is created based on the tomographic image data of the choroidal layer, and based on this classified data, the binary image data of the vascular network in the choroidal layer as obtained for each of the multiple windows of different sizes is selectively combined, while at a same time binary image data of choroidal network vessels separating out only the choroidal vessels is formed based on the binary image data of the shadows of the retinal vessels.

12. The image-processing method for an optical coherence tomography apparatus for selectively visualizing and analyzing a vascular network in a choroidal layer according to claim 11, wherein the method for obtaining data to be used in a quantitative evaluation of a shape of the choroidal vessels is such that, based on the binary image data of the choroidal network vessels separating out only the choroidal vessels, diameters of the choroidal vessels are estimated and diameter distribution data of the choroidal vessels is created based on estimated data, while at a same time a thickness of the vascular network in the choroidal layer is measured and a thickness map of the vascular network in the choroidal layer is created based on measured data.

* * * * *